US012527673B2

(12) United States Patent
Lenzi et al.

(10) Patent No.: US 12,527,673 B2
(45) Date of Patent: Jan. 20, 2026

(54) UNIFIED CONTROLLER FOR A POWERED KNEE PROSTHESIS

(71) Applicant: University of Utah Research Foundation, Salt Lake City, UT (US)

(72) Inventors: Tommaso Lenzi, Salt Lake City, UT (US); Lukas R. Gabert, Salt Lake City, UT (US); Liam Sullivan, Salt Lake City, UT (US); Marissa Ann Cowan, Salt Lake City, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 18/898,320

(22) Filed: Sep. 26, 2024

(65) Prior Publication Data

US 2025/0107905 A1 Apr. 3, 2025

Related U.S. Application Data

(60) Provisional application No. 63/541,705, filed on Sep. 29, 2023.

(51) Int. Cl.
*A61F 2/64* (2006.01)
*A61F 2/70* (2006.01)

(52) U.S. Cl.
CPC .......... *A61F 2/64* (2013.01); *A61F 2002/701* (2013.01); *A61F 2002/704* (2013.01)

(58) Field of Classification Search
CPC .. A61F 2/64; A61F 2/6607; A61F 2/68; A61F 2/70; A61F 2002/763; A61F 2002/7645
See application file for complete search history.

(56) References Cited

U.S. PATENT DOCUMENTS

| | | | |
|---|---|---|---|
| 8,623,098 B2 | 1/2014 | Goldfarb et al. | |
| 8,652,218 B2 | 2/2014 | Goldfarb et al. | |

(Continued)

FOREIGN PATENT DOCUMENTS

| | | | | |
|---|---|---|---|---|
| CA | 2762265 A1 * | 10/2001 | | A61F 2/64 |
| CN | 114795604 A | 7/2022 | | |

(Continued)

OTHER PUBLICATIONS

Alcock L., et al., "Biomechanical demands of the 2-step transitional gait cycles linking level gait and stair descent gait in older women," Journal of biomechanics, vol. 48, Issue 16, 2015, pp. 4191-4197.

(Continued)

*Primary Examiner* — Christie Bahena
(74) *Attorney, Agent, or Firm* — Workman Nydegger

(57) ABSTRACT

Disclosed are prosthetic systems comprising a powered knee prosthesis and a volitional controller configured to provide control of the prosthesis to the user. The prosthetic system may be configured to enable a user to walk on smooth and/or uneven terrain and to ascend and/or descend stairs. The volitional controller may be configured in a contact state when the prosthesis is in contact with a ground surface and a no contact state when the prosthesis is lifted from the ground surface. When in the contact state, the controller may output a knee torque signal for controlling the powered knee of the prosthesis. The knee torque signal may be based on a target knee torque determined by the knee orientation and the torque measured at the ankle of a prosthetic foot. When in the no contact state, the controller may output a knee torque signal based on a desired knee position.

15 Claims, 7 Drawing Sheets

(56) References Cited

U.S. PATENT DOCUMENTS

| | | | |
|---|---|---|---|
| 8,696,764 B2 | 4/2014 | Hansen et al. | |
| 8,852,292 B2 | 10/2014 | Ragnarsdottir et al. | |
| 9,192,487 B2 | 11/2015 | Flaven et al. | |
| 9,221,177 B2 | 12/2015 | Herr et al. | |
| 9,248,031 B2 | 2/2016 | Pusch et al. | |
| 9,443,203 B2 | 9/2016 | Young et al. | |
| 9,649,207 B2 | 5/2017 | Hahn et al. | |
| 9,687,377 B2 | 6/2017 | Han et al. | |
| 9,763,809 B2 | 9/2017 | Palmer et al. | |
| 9,975,249 B2 | 5/2018 | Herr et al. | |
| 10,369,023 B2 | 8/2019 | Simon et al. | |
| 10,575,971 B2 | 3/2020 | Herr et al. | |
| 2004/0167641 A1 | 8/2004 | Kawai et al. | |
| 2009/0265018 A1 | 10/2009 | Goldfarb et al. | |
| 2010/0241242 A1 | 9/2010 | Herr et al. | |
| 2012/0004736 A1* | 1/2012 | Goldfarb | A61F 2/60 623/25 |
| 2012/0221120 A1 | 8/2012 | Seyr et al. | |
| 2012/0226364 A1 | 9/2012 | Kampas et al. | |
| 2013/0310949 A1 | 11/2013 | Goldfarb et al. | |
| 2014/0364962 A1 | 12/2014 | Gregg et al. | |
| 2015/0066156 A1 | 3/2015 | Geyer et al. | |
| 2015/0127119 A1 | 5/2015 | Simon et al. | |
| 2015/0182354 A1* | 7/2015 | Bonnet | A61F 2/70 623/26 |
| 2016/0058582 A1 | 3/2016 | Lenzi et al. | |
| 2016/0302686 A1 | 10/2016 | Sigurpórsson et al. | |
| 2016/0338857 A1 | 11/2016 | Herr et al. | |
| 2017/0354529 A1 | 12/2017 | Han et al. | |
| 2019/0388247 A1 | 12/2019 | Goldfarb et al. | |
| 2023/0270570 A1 | 8/2023 | Hofmann et al. | |
| 2025/0107907 A1 | 4/2025 | Lenzi et al. | |
| 2025/0107908 A1 | 4/2025 | Lenzi et al. | |

FOREIGN PATENT DOCUMENTS

| | | | | |
|---|---|---|---|---|
| EP | 2849687 B1 | 7/2018 | | |
| WO | WO-2013067407 A1 * | 5/2013 | A61F 2/4657 |
| WO | WO-2016130745 A1 * | 8/2016 | A61F 2/60 |
| WO | 2022/087160 A1 | 4/2022 | |
| WO | 2022/087161 A1 | 4/2022 | |

OTHER PUBLICATIONS

Au S. et al., "Powered ankle-foot prosthesis to assist level-ground and stair-descent gaits," Neural Networks, vol. 21, Issue 4, 2008, pp. 654-666.

Best T. K. et al., "Data-Driven Variable Impedance Control of a Powered Knee-Ankle Prosthesis for Adaptive Speed and Incline Walking", IEEE Transactions on Robotics, 2023, pp. 19.

Ha K. H. et al., "Myoelectric control of a powered knee prosthesis for volitional movement during non-weight-bearing activities", 32nd Annual International Conference of the IEEE EMBS., 2010, pp. 3515-3518.

Hood S. et al., "Powered Knee and Ankle Prosthesis with Adaptive Control Enables Climbing Stairs with Different Stair Heights, Cadences, and Gait Patterns", IEEE Trans Robot, vol. 38, Issue 3, Jun. 2022, pp. 1430-1441.

Huang H. et al., "A strategy for identifying locomotion modes using surface electromyography," IEEE Trans Biomed Eng, vol. 56, Issue 1, Jan. 2009, pp. 65-73.

Neuman R. M., et al., "There are unique kinematics during locomotor transitions between level ground and stair ambulation that persist with increasing stair grade," Scientific Reports, vol. 13, Issue 1, 2023, 8576, pp. 11.

Non-Final Office Action received for U.S. Appl. No. 18/898,315, mailed on Nov. 14, 2024, 29 pages.

Peng J., et al., "Anticipatory kinematics and muscle activity preceding transitions from level-ground walking to stair ascent and descent," Journal of biomechanics vol. 49, Issue 4, 2016, pp. 528-536.

Shultz, A. H. et al., "Variable cadence walking and ground adaptive standing with a powered ankle prosthesis," IEEE Trans Neural Syst Rehabil Eng., vol. 24, Issue 4, Apr. 2016, pp. 495-505.

Non-Final Office Action received for U.S. Appl. No. 18/898,303, mailed on Dec. 19, 2024, 8 pages.

Non-Final Office Action received for U.S. Appl. No. 18/898,315, mailed on Mar. 19, 2025, 31 pages.

Translation of WO2011057792A1 (Year: 2011).

* cited by examiner

UNIFIED CONTROLLER FOR A POWERED KNEE PROSTHESIS

CROSS-REFERENCE TO RELATED APPLICATIONS

This application claims priority to and the benefit of U.S. Provisional Patent Application Ser. No. 63/541,705, filed Sep. 29, 2023 and titled "Unified Controller for a Powered Knee Prosthesis," the entirety of which is incorporated herein by reference.

STATEMENT REGARDING FEDERALLY SPONSORED RESEARCH

This invention was made with government support under W81XWH-21-1-0037 awarded by the Defense Health Agency, Medical Research and Development Branch, and R01 HD098154 awarded by the National Institutes of Health. The government has certain rights in the invention.

BACKGROUND

Technical Field

This disclosure relates to powered prosthetic limbs and controllers for operating powered prosthetic limbs.

Related Technology

Recent advances have improved the functionality of prosthetic limbs, including leg prostheses. Leg prostheses include lower leg prostheses configured to attach to the residual limb of a trans-tibial amputee and upper leg prostheses configured to attach to the residual limb of a trans-femoral amputee. Leg prostheses have been configured in size and shape to replace the functionality of the amputated limb.

Advances in leg prostheses include incorporation of newer lightweight materials, sensors that monitor movement of the user and the environment which enable users to adjust their gait or posture, adjustable settings, and improved energy storage and return that may reduce the fatigue experienced by the user. Despite this, ambulation with conventional passive prostheses is generally slow, inefficient, and unstable. Difficulty dealing with environmental barriers such as ramps, stairs, and uneven terrain often limits community ambulation. Limited mobility negatively affects independence and quality of life in individuals with lower limb amputations. Accordingly, there is an ongoing need for improved prosthesis control systems to meet the needs of individuals with above-knee amputations.

SUMMARY

Disclosed are embodiments of volitional controllers, volitional controller and prosthetic leg systems, and methods executable by the volitional controllers for operating a powered leg prosthesis. The volitional controller may comprise one or more processors and one or more hardware storage devices having instructions stored thereon that are executable by the one or more processors to cause the controller to output a knee torque signal for controlling a powered knee joint of a powered leg prosthesis.

The instructions may also cause the volitional controller to determine a knee orientation and an ankle torque and determine a target knee torque based on the knee orientation and ankle torque. When determining the target knee torque, the controller may not classify ambulation activity or switch between activity-specific controllers according to walking, stair ascent, or stair descent activities. The instructions may further cause the controller to determine a thigh orientation and a prosthetic knee velocity.

The target knee torque may be determined as the sum of a step-up torque and a biarticular torque. The biarticular torque may be proportional to the ankle torque and may be further proportional to a biarticular knee gain and a biarticular thigh gain. The biarticular knee gain may be dependent on a knee orientation and may be variable between a lower threshold and an upper threshold of the knee orientation. The biarticular thigh gain may be dependent on a thigh orientation and may be variable between a lower threshold and an upper threshold of the thigh orientation. The target knee torque may be further determined by the addition of a damping torque. The damping torque may be proportional to and opposite a prosthetic knee velocity.

The instructions may further cause the volitional controller to receive a ground state signal. The volitional controller may be configured in a contact state or a no contact state based on the ground state signal. The knee torque signal may be based on the target knee torque when the controller is in the contact state When the controller is in a no contact state the knee torque signal may be based on a desired knee orientation. The desired knee orientation may be determined by the sum of a minimum jerk trajectory and a synergistic orientation component. The synergistic orientation component may be determined as the product of a synergistic orientation and an adaptive gain.

The volitional controller may be connected with a powered prosthetic leg to form a powered knee and prosthetic leg system. The powered knee prosthesis may comprise a shank having a proximal and a distal end. A powered knee joint may be connected to the proximal end of the shank and a prosthetic foot may be connected to the distal end of the shank. A socket configured to receive the residual limb of a user may be connected to the powered knee joint. The powered knee prosthesis comprise may comprise one or more sensors, including a GRF sensor, an IMU sensor, and/or a torque sensor. The powered knee prosthesis may be configured to enable a user to walk on even and/or inclined surfaces and to ascend and/or descend stairs.

The disclosure may comprise a method for controlling a powered knee prosthesis, the method comprising determining a knee orientation and an ankle torque, determining a target knee torque based on the knee orientation and ankle torque, and outputting a knee torque signal for controlling a powered knee joint of the powered knee prosthesis. The method may further comprise determining a thigh orientation and a prosthetic knee velocity and may comprise configuring a volitional controller in a contact state or a no contact state and basing the knee torque signal on the target knee torque when the volitional controller is in the contact state.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

DETAILED DESCRIPTION

Introduction

Figure 1:
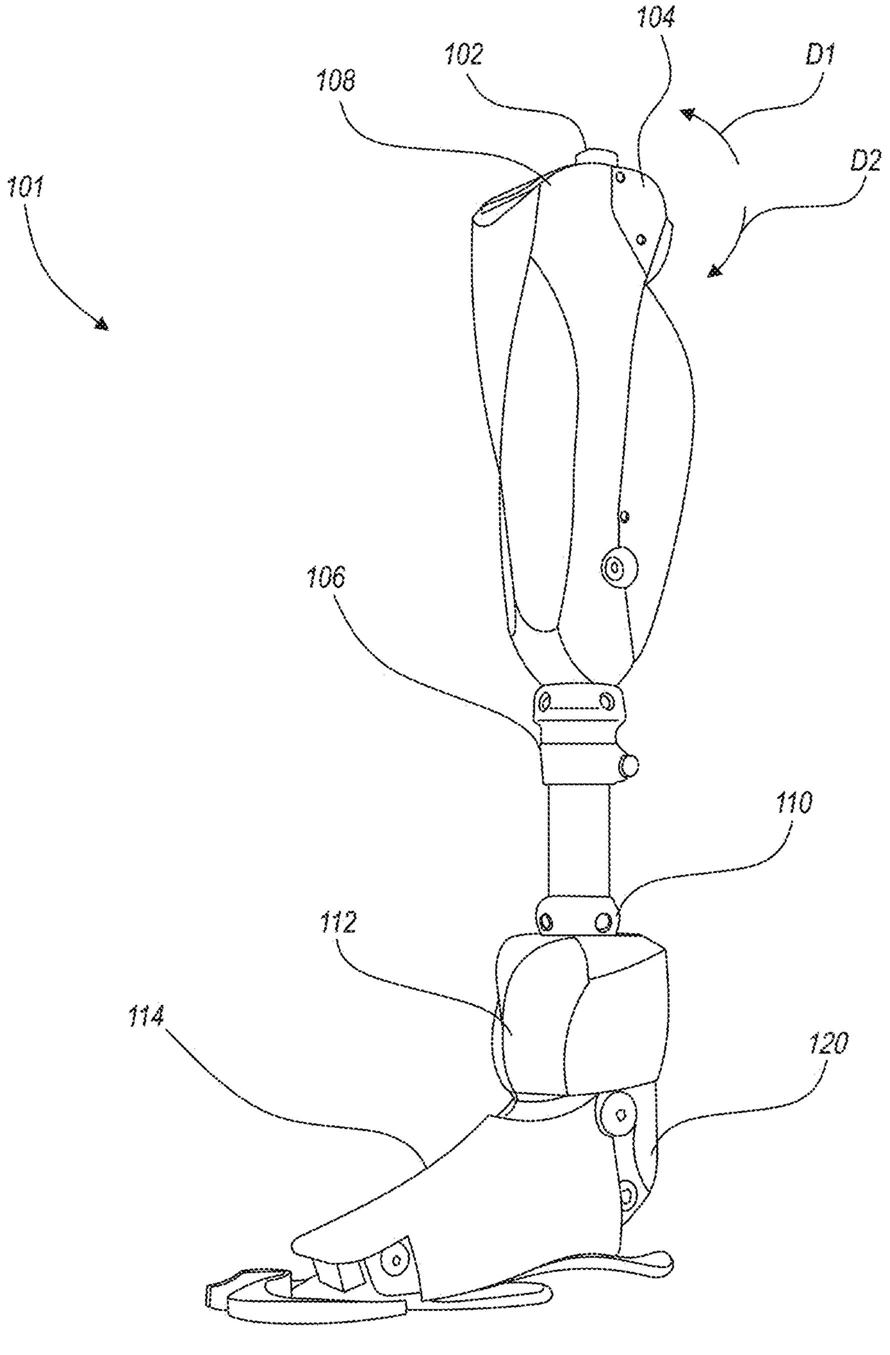
FIG. 1 illustrates an exemplary powered prosthetic leg.

Ambulation with conventional passive prostheses is generally slow, inefficient, and unstable. Difficulty dealing with environmental barriers such as ramps, stairs, and uneven terrain often limits ambulation. Limited mobility negatively affects independence and quality of life in individuals with lower limb amputations and can partly explain the high incidence of depression in this population. Improved prosthesis technologies are necessary to meet the needs of individuals with above-knee amputations.

Powered lower-limb prostheses have potential to improve mobility for amputees. Using embedded actuators, powered prostheses may replicate the biomechanical functions of the missing biological leg. To accomplish this goal, powered prostheses need controllers that can coordinate the movements of the prosthetic joints with the user's residual and sound limbs, seamlessly adapting to the user's intended ambulation activity while dealing with the variability of the environment. Most powered prostheses aim to classify the user's intended ambulation activity (e.g., walking, stair climbing) in real-time, and then switch to a controller dedicated to that specific ambulation activity.

Activity classification is typically performed using machine learning. To train the machine learning algorithms, researchers have proposed using labelled data collected while amputee or nonamputee subjects ambulate in a laboratory environment which includes level-ground walking, stairs, and ramps. The accuracy of the classification depends on the amount of data used for training, and can be improved using different kinds of sensors, including electromyography, sonomyography, range sensors, or cameras, in addition to prosthesis joint position and torque. However, the many misclassifications are often made by such machine learning models. A prosthesis user may take thousands of steps in a day, and any misclassification of the user's intended ambulation activity can cause the prosthesis to perform a different movement than the user expects, increasing the likelihood of falls and injuries. Therefore, nearly perfect accuracy is necessary for this "classify-and-switch" approach to succeed in real life.

Disclosed is a unified controller for powered knee prostheses that seamlessly adapts to walking, stair ascent, and stair descent without explicit classification of the user's intended ambulation activity. The proposed controller continuously adapts the behavior of the powered prosthesis based on the movements of the user's residual thigh and the interaction of the prosthesis with the ground. Continuous adaptation is accomplished without making any assumptions about the user's intended activity (e.g., walk, climb stairs) or the characteristics of the environment (e.g., stair height). As a result, the proposed controller does not need to classify the intended ambulation activity or switch between activity specific controllers. Specifically, the proposed controller does not separate the movement into discrete, sequential phases, nor does it use a continuous phase evolution. A controller with these characteristics may enable powered prostheses to support natural ambulation, improving mobility for individuals with above-knee amputations.

Definitions

As used herein, the term "volitional controller" may refer to a device or group of devices configured to coordinate the performance of an electric motor. The volitional controller may be configured to provide control of a user to a prosthetic limb. The volitional controller may comprise one or more processors and/or one or more hardware storage devices. The volitional controller may comprise a computer or other device configured to algorithmically process incoming signals to operate a powered motor.

As used herein, the term "prosthetic limb" may refer to an artificial limb that replaces a missing body part. The prosthetic limb may primarily refer to a prosthetic leg configured to be attached to the upper leg of a trans-femoral amputee.

As used herein, the term "powered prosthesis," "powered prosthetic leg," or related terms may refer to a prosthetic limb that includes one or more electrical or powered components, such as electrical motors or sensors. The terms may also refer to a prosthetic limb comprising a powered or motored joint.

As used herein, the term "residual limb" may refer to the remaining part of a limb after an amputation. It may refer to the upper leg of a trans-femoral amputee.

As used herein, the term "wearable" or "wearable device" may refer to a device which is configured to be carried on the prosthesis and/or the body of the user.

As used herein, the term "gait cycle" may refer to the repetitive pattern of movement that occurs when a person walks or climbs a set of stairs.

As used herein, the term "ground surface" may refer to a surface with which the prosthetic foot of the powered prosthetic leg interacts during the gait cycle.

As used herein, the term "ground reaction force" (GRF) may refer to a force exerted on the prosthetic limb by the ground surface. The GRF sensor may measure a ground reaction force as the user places their weight on the prosthetic limb.

As used herein, the term "electromyography" (EMG) may refer to measurement of the electrical activity in the muscles and/or nerves that control the muscles.

As used herein, the term "inertial measurement unit" (IMU) may refer to a device that measures a body's specific force, angular rate, and/or orientation of the body. The IMU may incorporate accelerometers, gyroscopes, and/or magnetometers.

Powered Prosthetic Leg Components and Sensor Signals

FIG. 1 illustrates a powered prosthetic leg 101 that may comprise one or more powered components configured to be operated with the controller described herein. The powered prosthetic leg 101 may comprise a distally-extending shank 106 having a proximal end 108 and a distal end 110, the shank 106 being configured to support the weight of a user. The distal end 110 of the shank 106 may be connected to a prosthetic foot 114. The prosthetic foot 114 may be a passive prosthetic foot, in that the prosthetic foot 114 does not comprise any powered components. Alternatively, the prosthetic foot 114 may be an active prosthetic foot 114 that may comprise one or more powered components configured to facilitate the walking and climbing movement of the user, such as a powered ankle joint. The prosthetic foot 114 may be connected to the distal end 110 of the shank 106 by a distal adapter 112 (e.g., a pyramid adapter) configured to facilitate connection between the prosthetic foot 114 and the shank 106. The distal adapter 112 may be detachable from the shank 106 to allow different configurations of a prosthetic foot 114 to be attached to the powered prosthetic leg 101.

The powered prosthetic leg 101 may comprise a powered knee prosthesis. Specifically, the powered prosthetic leg 101 may comprise a powered knee joint 104 that may be configured to rotate the shank 106 along at least one axis in directions D1 and D2. The powered knee joint 104 may be located at or near the proximal end 108 of the shank 106 and may be located at a position that would correspond to the user's knee before amputation. The powered knee joint 104 may be configured to provide various levels of torque to enable the shank 106 of the powered prosthetic leg 101 to rotate relative to the socket 218 and provide support to the user. The powered knee joint 104 may provide sufficient torque to lift the user and may provide a torque of approximately 10 Nm, approximately 20 Nm, approximately 30 Nm, approximately 40 Nm, approximately 50 Nm, approximately 60 Nm, approximately 70 Nm, or more than approximately 70 Nm, or may provide a torque within a range having any two of the foregoing as endpoints The powered prosthetic leg 101 may be configured to receive the residual limb 216 (see FIG. 2) of a user. Specifically, the powered prosthetic leg 101 may comprise a socket 218 (see FIG. 2) configured to receive the residual limb. The socket 218 may be configured to receive the residual limb of a trans-femoral amputee (wherein the leg has been amputated above the knee), such that the socket 218 is configured to receive the residual limb 216 of the upper leg of a user. The socket 218 may be formed about the residual limb 216 of the user. For example, the socket 218 may be formed through a molding process such that the socket 218 forms a comfortable and tight fit with the user's residual limb 216. The socket 218 may be attached to an proximal adapter 102 extending from the powered knee joint 104.

In this manner, the powered knee joint 104 may be configured to, at least in part, replace the knee joint of the amputee user. The powered knee joint 104 may rotate to enable the powered prosthetic leg 101 to flex (wherein the shank 106 is rotated in direction D1) and extend (wherein the shank 106 is rotated in direction D2). This flexion and extension may enable the powered prosthetic leg 101 to provide a more natural ambulatory motion during walking by the user and may be useful in assisting the user to traverse even or uneven terrain as well as ascending or descending stairs.

The powered prosthetic leg 101 may comprise metals, such as aluminum, steel, stainless steel, or titanium, or may comprise polymers, such as carbon fiber, glass fiber, or other lightweight and rigid plastics, or may comprise a composite material.

A volitional controller may be configured to adjust the behavior of the powered prosthetic leg 101, particularly of the powered knee joint 104. The volitional controller may be connected to the powered prosthetic leg 101 to form a powered knee and prosthetic leg system 100. The volitional controller may be attached to a portion of the powered knee and prosthetic leg system 100, such as the powered prosthetic leg 101. For example, the volitional controller may be attached to or disposed within the shank 106.

The volitional controller may comprise a computer or other hardware device configured to receive one or more inputs and to provide an output of a target torque. The volitional controller may comprise one or more processors and may be connected to one or more hardware storage devices that include instructions for operating the powered knee joint 104. In some embodiments, the volitional controller may comprise a computer system.

The volitional controller may comprise one or more hardware storage devices. The one or more hardware storage devices may be configured to store signal data measured by the one or more sensors. The one or more hardware storage devices may be configured to store instructions to be implemented by the volitional controller. The one or more hardware storage devices may comprise a computer readable storage medium that includes volatile and non-volatile, removable and non-removable media, implemented with any technology for the storage of information such as computer readable instructions, data structures, program modules, or other data. Computer readable storage media includes, but is not limited to, a non-transitory machine readable storage medium, such as RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which may be used to store the desired information and described technology.

The volitional controller may be connected to one or more sensors attached to or disposed about the powered prosthetic leg 101. The one or more sensors may send signals to the volitional controller that may be used to activate the powered knee joint 104, determine an orientation or velocity of the components of the powered prosthetic leg 101, and/or determine a target torque to be exerted by the powered components of the powered prosthetic leg 101, such as the powered knee joint 104.

The one or more sensors may be configured to determine when the powered knee and prosthetic leg system 100 is in contact with a ground surface. The powered knee and prosthetic leg system 100 may comprise a ground reaction force (GRF) sensor that may measure the amount of force (referred to as a "ground reaction force") placed on the powered prosthetic leg 101 to support the user. In at least one aspect, the GRF sensor may be used to determine if the powered prosthetic leg 101 is in contact with the ground. The GRF sensor may be disposed on or connected to the powered prosthetic leg 101. The GRF sensor may be disposed within the distal adapter 112 connecting the prosthetic foot to the shank 106. In other embodiments, the GRF sensor may be disposed within or attached to the prosthetic foot 114 or to the shank 106. In some embodiments, the GRF sensor may be attached to the proximal adapter 102 or may be attached to or disposed within the socket 218. The GRF sensor may comprise a wearable force plate that measures the force between the powered prosthetic leg 101 and a ground surface and may indicate when the powered prosthetic leg 101 is in contact with or off the ground surface.

The one or more sensors may be configured to provide signals used to determine the orientation of the residual limb of the user, the orientation of the shank 106, and/or the orientation of the prosthetic foot 114. The powered knee and prosthetic leg system 100 may comprise one or more inertial measurement unit (IMU) sensors. The IMU sensor(s) may be configured to measure motion and/or orientation of the residual limb 216 and one or more components of the powered prosthetic leg 101. For example, the IMU signals may be used to determine the thigh and knee orientations 220, 222 described below. The IMU sensor(s) may be attached to various parts of the powered prosthetic leg 101, the socket 218, and/or the user. For example, the system 100 may comprise a first IMU sensor attached to the socket 218 or the residual limb 216 of the user and a second IMU sensor attached to the powered prosthetic leg 101, such as at the shank 106 or the prosthetic foot 114. In this way, the IMU signals from both of the IMU sensors may provide information necessary to determine the relative orientation between the residual limb 216 and the powered prosthetic leg 101.

Additionally, or alternatively, an IMU sensor may be attached to the prosthetic foot 114 at or near the proximal end of the foot 114 near ankle joint 120 and in line with the shank 106. In this manner, the IMU sensor may measure the rotation of the prosthetic foot 114 as well as the movement of the distal end 110 of the shank 106.

In other embodiments, the system 100 may comprise only one IMU sensor. The one IMU sensor may be disposed at the proximal end 108 of the powered prosthetic leg 101. Because the position of the proximal end 108 of the powered prosthetic leg 101 is determined by movement of the residual limb 216 and because the one IMU sensor will rotate relative to the powered knee joint 104 along with the shank 106 of the powered prosthetic leg 101, the one IMU sensor may provide the orientation of the residual limb 216 as well as the orientation of the powered prosthetic leg 101.

The one or more sensors may be configured to measure the activation of one or more muscles of the user. In such instances, the activation of the powered prosthetic leg 101 may be dependent on the activation the one or more muscles of the user. For example, the one or more sensors may comprise an electromyography (EMG) sensor comprising an electrode configured to measure the activation of an EMG signal source, such as a muscle in the residual limb. The EMG signal may be amplified before it is received by the volitional controller. The powered prosthetic leg 101 may activate only when the EMG signal source activates. In this manner, control of the powered prosthetic leg 101 may be more intuitive to the user, such that the user may replicate movements similar to pre-amputee walking movements to activate the powered prosthetic leg 101.

The one or more sensors may be configured to measure the torque at one or more joints of the powered prosthetic leg 101. That is, a torque sensor (such as a torque meter) may be configured to measure a torque at the joints of the powered prosthetic leg 101, including the ankle joint 120 of the prosthetic foot 114. The ankle joint 120 may be a passive ankle joint 120, such that the ankle joint 120 of the powered prosthetic leg 101 may flex (e.g., in dorsiflexion or plantarflexion) without the intervention of a powered component at the ankle joint 120. The ankle joint 120 may comprise resistive elements, such as a blade that may store and/or release energy to compress and extend so as to dampen and smooth the gait phase of the user during ambulation. The compression or extension may be measured to provide a corresponding or equivalent torque of the ankle joint 120. In other embodiments, the ankle joint 120 may comprise a powered ankle joint that may output a torque to support and lift the user. The powered ankle joint may similarly comprise a torque sensor for measuring the actual torque exhibited at the ankle joint 120.

The powered knee and prosthetic leg system 100 may comprise other sensors that may be used to determine an orientation of the components of the powered prosthetic leg 101, to further measure the movement of the user, or to otherwise assist in navigating the surrounding terrain of the user. For example, the one or more sensors may be used to identify obstacles, evaluate the incline of the ground surface, or determine if the ground surface is smooth or uneven. The one or more sensors may comprise cameras, sonomyography sensors, range sensors, or other sensors configured for these purposes.

The one or more sensors may be configured to frequently provide measurement signals to the volitional controller. For example, one or multiple of the one or more sensors may provide measurement signals to the volitional controller at a rate of 1, 10, 100, 1000, or more than 1000 signals per second. In this manner, the volitional controller may continuously adapt to the movement and orientation of the user and/or the powered prosthetic leg 101 to provide improved performance during motion of the powered prosthetic leg 101.

The volitional controller may be attached to the one or more sensors, including the GRF sensor, IMU sensor(s), and/or torque sensor. The volitional controller may be connected to the one or more sensors by wiring that extends from the sensors to the controller. The wiring may extend along an exterior of the socket 218 and/or the powered prosthetic leg 101, but preferably extends within the socket 218 and the powered prosthetic leg 101 so as to prevent environmental obstacles from snagging the wiring.

Gait Cycle

Figure 2:
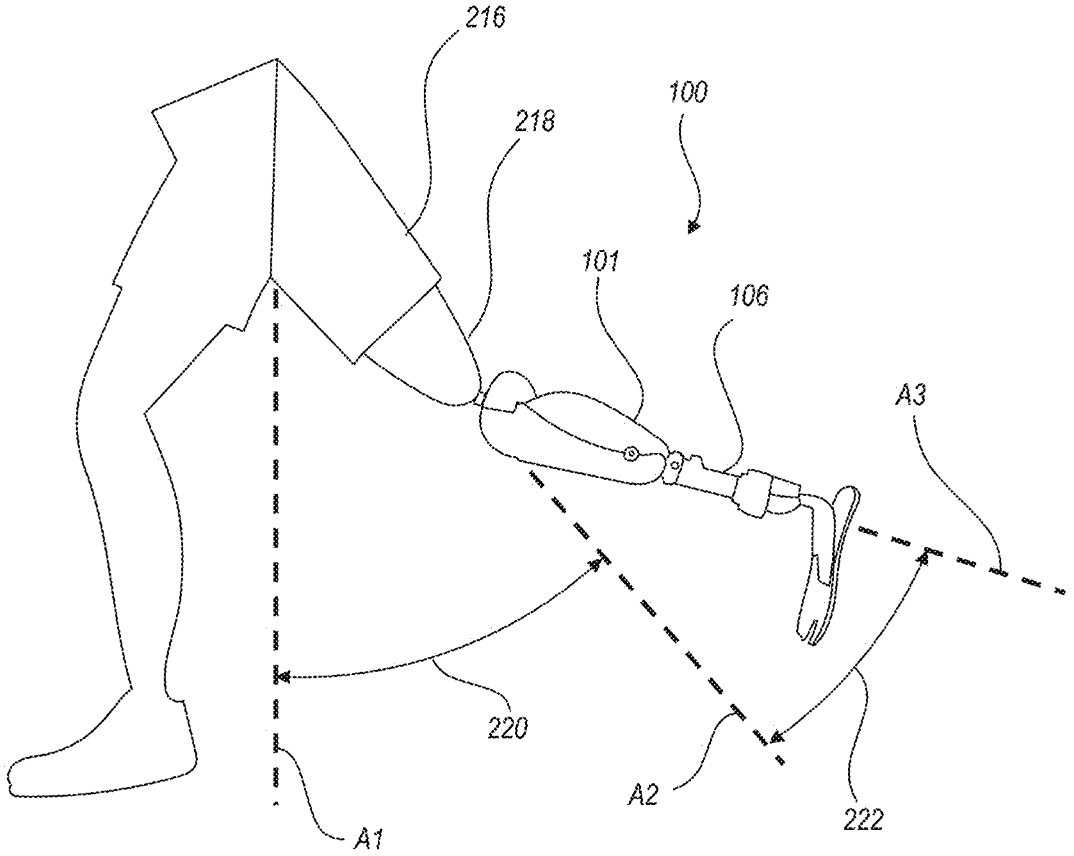
FIG. 2 illustrates the powered prosthetic leg attached to the residual limb of a user.

FIG. 2 illustrates a user during walking movements, the user having the volitional controller and the powered prosthetic leg 101 attached to the residual limb 216 as part of a powered knee and prosthetic leg system 100. Also illustrated are axes A1, A2, and A3 as well as orientations 220 and 222 that will be useful in describing the operation of the volitional controller to manipulate the powered prosthetic leg 101. An orientation axis A1 may refer to a line extending in the direction of gravity or may refer to a direction of the normal force acting through the user's non-amputated leg or another prosthetic leg of user. A thigh axis A2 may refer to a line passing through the center of the user's upper leg or thigh, or a line passing through the center of the socket 218. The thigh orientation 220 (i.e., $\theta_{Thigh}$) may refer to the angle between the thigh axis A2 and the orientation axis A1. Finally, a shank axis A3 may refer to a line passing through the center of the shank 106. The knee orientation 222 (i.e., $\theta_{Knee}$) may refer to the angle between the thigh axis A2 and the shank axis A3. As used herein, the thigh orientation 220 is positive behind (posterior to) the user and negative when in front of (anterior to) the user. Similarly, the knee orientation 222 is positive during flexion and approaches a value of 0 degrees at full extension.

Signals from the one or more sensors, the determined thigh orientations, and/or the determined knee orientations may be stored in the one or more hardware storage devices. For example, the one or more hardware storage devices may store received measurement signals and/or determined orientations from the 1, 2, 3, 4, 5, or more than 5 seconds. A prosthetic knee velocity (i.e., $\dot{\theta}_{Knee}$) may be measured as the change in the knee orientation over time (e.g., measured in degrees per second). The prosthetic knee velocity may be determined as the change in knee orientation over the last 2, 3, 4, 5, 10, 50, 100, 500, 1000 determined knee orientations, or may be determined over a set of knee orientations within a range having any two of the foregoing as endpoints.

By way of explanation, the gait cycle of any one of the user's legs may generally comprise two phases during walking movements: stance phase and swing phase. Stance phase may begin as the user touches the heel of the foot (e.g., the prosthetic foot 114) to the ground (referred to as "heel strike") and progresses through mid-stance, terminal stance, and pre-swing as the user leans through the leg. Swing phase begins at toe-off as the user lifts the foot (e.g., the prosthetic foot 114) off the ground and continues through terminal swing (i.e., through mid-swing and terminal swing) until the user places their foot back on the ground at heel strike. Thus, FIG. 2 may illustrates the user at a moment wherein the powered prosthetic leg 101 is near the beginning of swing phase.

Determination of the Target Knee Torque

Figure 3:
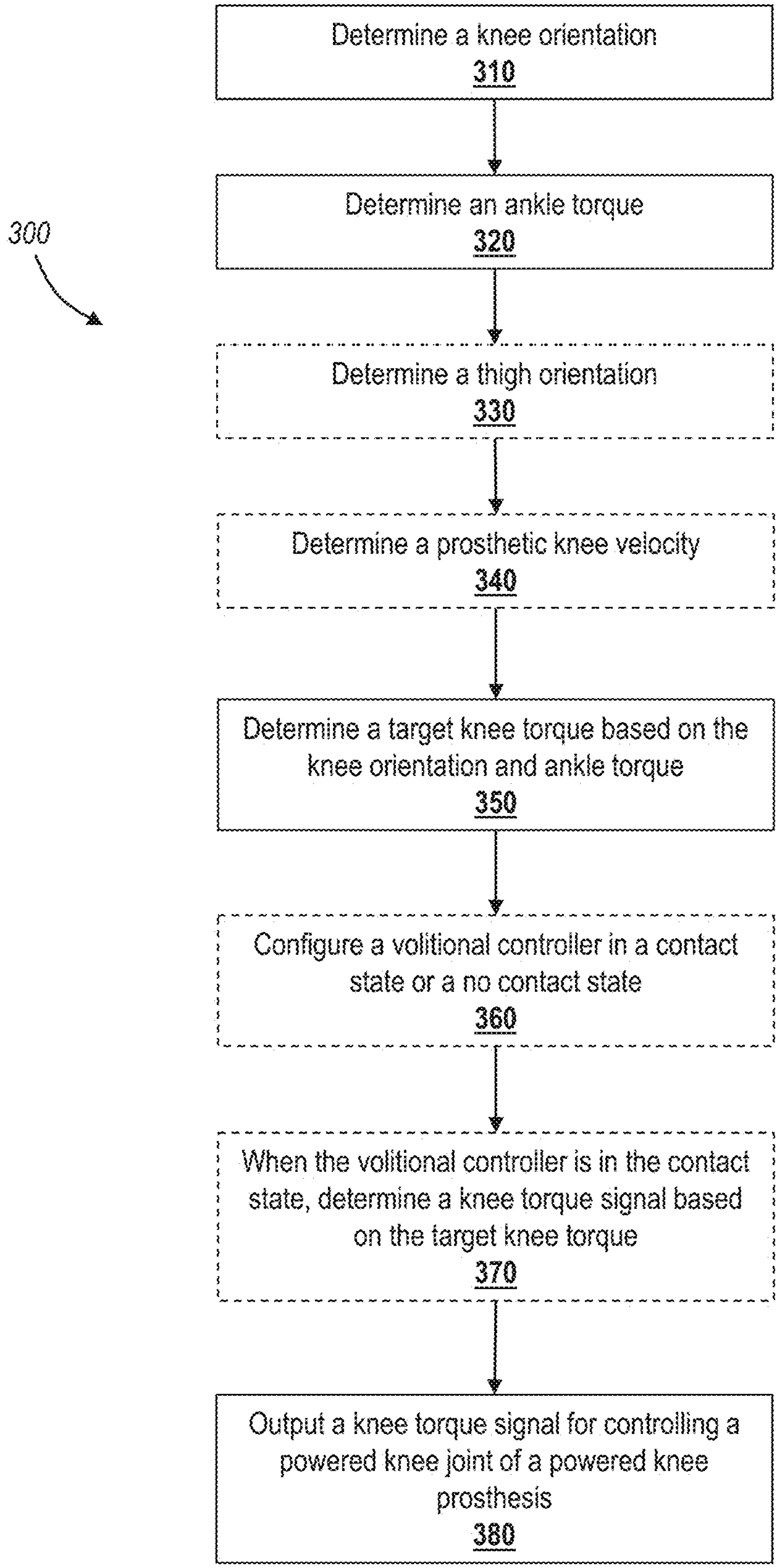
FIG. 3 illustrates a method for controlling a powered knee of the powered prosthetic leg.

FIG. 3 illustrates a method 300 comprising instructions that may be implemented by the volitional controller to regulate the behavior of the powered prosthetic leg 101. The instructions may cause the volitional controller to determine a knee orientation 310 and to determine an ankle torque 320. The determination of the knee orientation 222 and ankle torque 450 (i.e. $T_{Ankle}$) (see FIG. 4) may be based on the measured signals obtained by the one or more sensors, such as the one or more IMU sensors or a torque sensor. The instructions may further cause the volitional controller to optionally determine a thigh orientation 330 and determine a prosthetic knee velocity 340. The volitional controller may then determine a target knee torque based on the knee orientation and ankle torque 350. Determination of the target knee torque 410 may be further based on the thigh orientation 220 and the prosthetic knee velocity 408.

In some embodiments, the instructions may cause the volitional controller to be configured in a contact state or a no contact state 360. When the volitional controller is in the contact state, the knee torque signal may be determined based on the target knee torque 370. Finally, the instructions may cause the volitional controller to output a knee torque signal for controlling a powered knee joint 104 of a powered knee prosthesis 380. The instructions may be performed without requiring the volitional controller to classify ambulation activity or switch between activity-specific controllers according to walking, stair ascent, or stair descent activities.

The volitional controller may comprise or may be connected to a finite-state machine configured to adjust the state of the volitional controller. The volitional controller may comprise a contact state and a no contact state. The contact state and the no contact state may be correlated with the stance phase and the swing phase, respectively, of the gait cycle of the powered prosthetic leg 101. That is, during stance phase when the powered prosthetic leg 101 is in contact with the ground surface, the volitional controller may be configured in the contact state and during swing phase when the powered prosthetic leg 101 is not in contact with the ground surface the volitional controller may be configured in the no contact state. The contact state and no contact state may also be associated with actions that do not strictly form part of the walking gait cycle, which may include ascending and descending stairs or other actions performed by the legs (including the powered prosthetic leg 101) of the user.

The logic and/or processing of the finite-state machine may be formed as part of the volitional controller or may be formed as part of another circuit or controller configured to alter the state of the volitional controller. The finite-state machine may be configured to receive a ground state signal from a GRF sensor to determine whether the powered prosthetic leg 101 is in contact with the ground surface (and therefore in stance phase). The finite-state machine may be configured to configure the volitional controller in stance state when the ground state signal rises above an upper GRF threshold and to configure the volitional controller in swing state when the ground state signal falls below a lower GRF threshold.

The upper GRF threshold may be greater than the lower GRF threshold. The upper GRF threshold may be set to a value within a range from approximately 40 N to approximately 160 N, or from approximately 50 N to approximately 155 N, or from approximately 60 N to approximately 150 N, or from approximately 70 N to approximately 145 N, or from approximately 80 N to approximately 140 N, or from approximately 90 N to approximately 135 N, or from approximately 100 N to approximately 130 N, or from approximately 110 N to approximately 135 N, or from approximately 115 N to approximately 120, or within a range having any two of the foregoing as endpoints. Similarly, the lower GRF threshold may be set to a value within a range from approximately 10 N to approximately 90 N, or from approximately 20 N to approximately 80 N, or from approximately 25 N to approximately 70 N, or from approximately 30 N to approximately 60 N, or from approximately 35 N to approximately 50 N, or may be set to approximately 40 N, or may be set within a range having any two of the foregoing as endpoints. The upper and lower GRF thresholds may be determined by the weight and/or age of the user. For example, the one or both of the GRF thresholds may be greater for a person weighing more than 200 pounds than for a person weighing between 120 and 150 pounds.

For example, the upper GRF threshold may be set at 60 N and the lower GRF threshold may be set at 20 N. At heel strike, when a user places a load on the powered prosthetic leg 101, the GRF sensor may then provide a ground state signal above 60 N such that the finite-state machine configures the volitional controller in stance state. The volitional controller may then remain in stance state until the ground state signal falls below the lower GRF threshold. That is, the volitional controller then remains in stance state while the ground state signal falls below the upper GRF threshold until the ground state signal falls below the lower GRF threshold. At pre-swing, the user may remove the load from the powered prosthetic leg 101 such that the ground state signal falls below the lower GRF threshold and the finite-state machine configures the volitional controller in swing state until the load on the powered prosthetic leg 101 again rises above the upper GRF threshold.

Contact State

Figure 4:
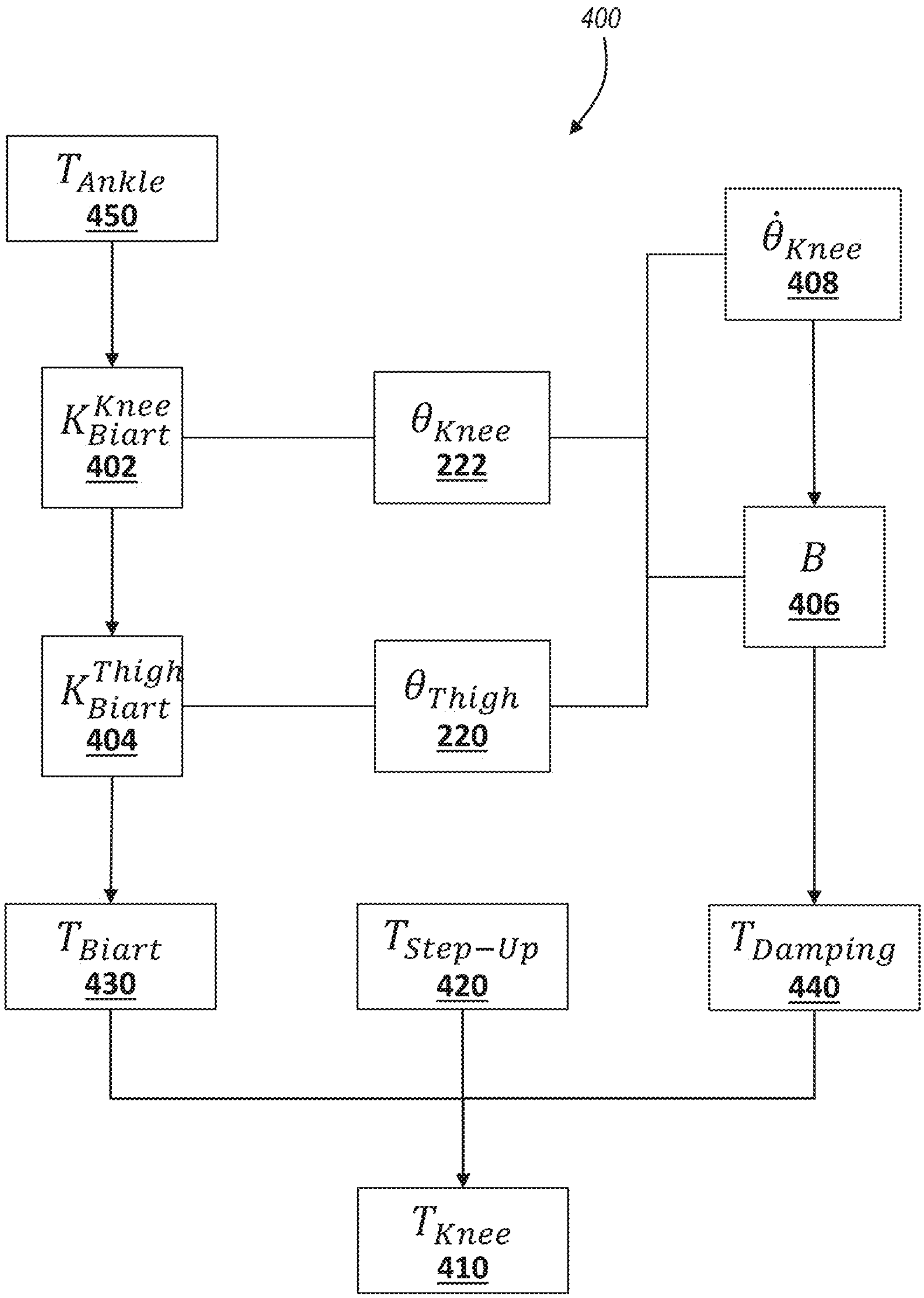
FIG. 4 illustrates a schematic of a process for determining a target knee torque by a volitional controller connected to the powered prosthetic leg.

FIG. 4 illustrates a schematic 400 of the process by which the target knee torque 410 (i.e., $T_{Knee}$) may be determined. The target knee torque 410 can be determined by the sum of at least two torque components comprising a step-up torque 420 (i.e., $T_{step\text{-}Up}$) and a biarticular torque 430 (i.e., $T_{Biart}$), as in the following relationship: $T_{Knee}=T_{step\text{-}Up}+T_{Biart}$. In this manner, the powered knee joint 104 may be configured to apply a torque and rotate the shank 106 in a positive direction (direction D1) to flex the powered knee joint 104 or to apply a torque and rotate the shank 106 in a negative direction (direction D2 opposite direction D1) to extend the powered knee join 104. The torque components may be determined from the input of measurement signals from the one or more sensors, such as the ground state signals, IMU signals, EMG signals, torque signals, or other measurement signals.

Figure 5:
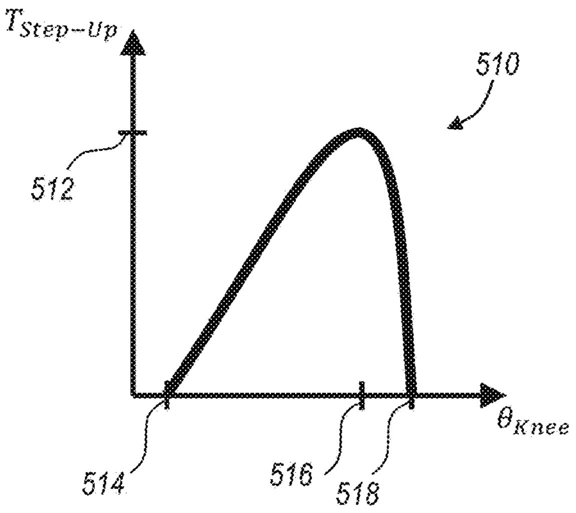
FIG. 5 illustrates the variability of the step-up torque with respect to the knee orientation.

FIG. 5 illustrates the relationship 510 between the step-up torque 420 and the knee orientation 222, such that the step-up torque 420 is determined based on the knee orientation 222. As shown, the step-up torque 420 follows a bell-shaped curve between a lower knee orientation threshold 514 and an upper knee orientation threshold 518. The step-up torque 420 may function to mimic the biomechanical knee torque during stair ascent and sit-to-stand transitions. The step-up torque 420 may extend from 0 Nm to a maximum torque 512 between the lower knee orientation threshold 514 and the upper knee orientation threshold 518. The lower knee orientation threshold 514 may correspond to the knee orientation 222 at toe-off (i.e., $\theta_{Knee}^{End}$) at the end of stance phase and the upper knee orientation threshold 518 (i.e., $\theta_{Knee}^{Toe\text{-}On}$) may correspond to the knee orientation at heel strike or other moment when the prosthetic foot 114 first contacts the ground surface (i.e. toe-on).

The maximum torque (i.e., $T_{Knee}^{Max}$) of the step-up torque 420 may be dependent on the upper knee orientation threshold 518, according to the following relationship: $T_{Knee}^{Max}=M_1\cdot\theta_{Knee}^{Toe\text{-}on}$. Thus, the maximum torque of the step-up torque 420 may be determined as the product of the upper knee orientation threshold 518 and a first multiplier (i.e., $M_1$). The first multiplier may be a constant, and may be set within a range from approximately 0.5 to approximately 2.5, or from approximately 1.0 to approximately 2.0, or from approximately 1.1 to approximately 1.8, or from approximately 1.2 to approximately 1.5, or may be set within a range having any two of the foregoing as endpoints, or may otherwise be set or calibrated according to the needs of the user.

The step-up torque 420 may be set to the maximum torque when the knee orientation 222 is at a maximum torque knee orientation 516 (i.e., $\theta_{Knee}^{T_{Max}}$). The maximum torque knee orientation 516 may be set between the lower and upper knee orientation thresholds 514, 518. Specifically, the maximum torque knee orientation 516 may be determined as follows: $\theta_{Knee}^{T_{Max}}=M_2\cdot(\theta_{Knee}^{Toe\text{-}On}-\theta_{Knee}^{End})+\theta_{Knee}^{End}$. A second multiplier (i.e., $M_2$) may be set to a value between 0 and 1 so as to set the maximum torque knee orientation 516 at a proportional distance between the lower and upper knee orientation thresholds 514, 518. The second multiplier may be set to a value of approximately 0.50, approximately 0.55, approximately 0.60, approximately 0.65, approximately 0.70, approximately 0.75, approximately 0.80, approximately 0.85, approximately 0.90, or approximately 0.95, or may be set within a range having any two of the foregoing as endpoints. Thus, the maximum torque knee orientation 516 may be determined as a proportion distance between the lower and upper knee orientation thresholds 514, 518.

The step-up torque 420 may form a polynomial relationship with respect to the knee orientation 222, such as a binomial relationship, a trinomial relationship, or other polynomial relationship. A portion of the illustrated step-up torque curve may be linear between the lower knee orientation threshold 514 and the maximum torque knee orientation 516, or between the maximum torque knee orientation 516 and the upper knee orientation threshold 518.

The biarticular torque 430 may provide flexion torque that increases with the measured ankle torque 450. The biarticular torque 430 may be proportional to the ankle torque 450, as measured by a torque sensor. Thus, as the torque 450 at the ankle increases (i.e., with increasing ankle plantarflexion), so too may the biarticular torque 430. The biarticular torque may be further proportional to multiple gain coefficients, including a biarticular knee gain 402 (i.e., $K_{Biart}^{Knee}$) and a biarticular thigh gain 404 (i.e., $K_{Biart}^{Thigh}$). Thus, the biarticular torque 430 may be defined by the following relationship: $T_{Biart}=K_{Biart}^{Knee}\cdot K_{Biart}^{Thigh}\cdot T_{Ankle}$. FIG. 4 illustrates that the biarticular knee gain 402 may be related to the knee orientation 222 and the biarticular thigh gain 404 may be related to the thigh orientation 220. Specifically, the value of the biarticular knee gain 402 may depend on the knee orientation 222 and the biarticular thigh gain 404 may depend on the thigh orientation 220.

Figure 6A:
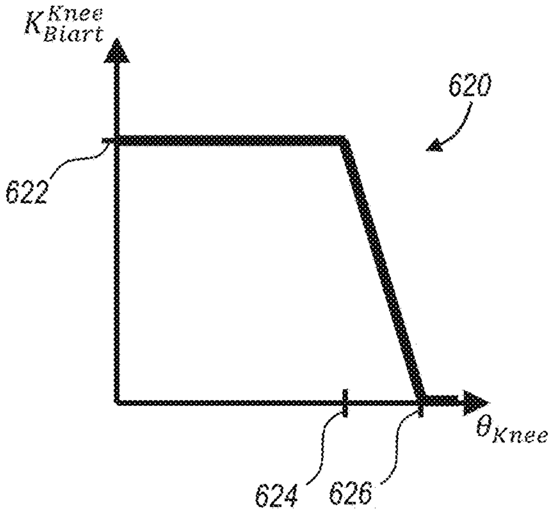
FIGS. 6A-6B illustrate the variability of gain values used to calculate biarticular torque.

FIG. 6A shows the relationship 620 between the biarticular knee gain 402 and the knee orientation 222 and illustrates that the value of the biarticular knee gain 402 may be dependent on the measured knee orientation 222. In particular, the biarticular knee gain 402 may be variable between a lower threshold 624 and an upper threshold 626 of the knee orientation 222. The biarticular knee gain 402 may be at the maximum value 622 when the knee orientation 222 is at or below the lower threshold 624 and may be at the minimum value when the knee orientation 222 is at or above the upper threshold 626. For example, the maximum value 622 may be approximately 1.0 and the minimum value may be approximately 0, such that the biarticular knee gain 402 exhibits a value from approximately 0 to approximately 1.0. The maximum value 622 of the biarticular knee gain 402 may not necessarily be 1.0, but may be a value corresponding to the particular characteristics and/or dimensions of the powered prosthetic leg 101.

The lower threshold 624 may be set within a range from approximately 15 degrees to approximately 45 degrees, or from approximately 20 degrees to approximately 40 degrees, or from approximately 22 degrees to approximately 38 degrees, or from approximately 25 degrees to approximately 35 degrees, or from approximately 28 degrees to approximately 32 degrees, or may be set to approximately 30 degrees, or may be set within a range having any two of the foregoing as endpoints. The upper threshold 626 may be set within a range from approximately 25 degrees to approximately 55 degrees, or from approximately 30 degrees to approximately 50 degrees, or from approximately 32 degrees to approximately 48 degrees, or from approximately 35 degrees to approximately 45 degrees, or from approximately 38 degrees to approximately 42 degrees, or approximately 40 degrees, or may be set within a range having any two of the foregoing as endpoints. For example, the lower and upper thresholds 624, 626 may be set to approximately 30 degrees and approximately 40 degrees, respectively.

The biarticular knee gain 402 may be linearly related to the knee orientation 222 between the upper and lower thresholds 626, 624. Alternatively, the biarticular knee gain 402 may be linearly related to the knee orientation 222 over only a portion of the range between the upper and lower thresholds 626, 624 or may have another relationship with the knee orientation 222, such as an exponential or logarithmic relationship, or a binomial, trinomial, or other polynomial relationship.

Figure 6B:
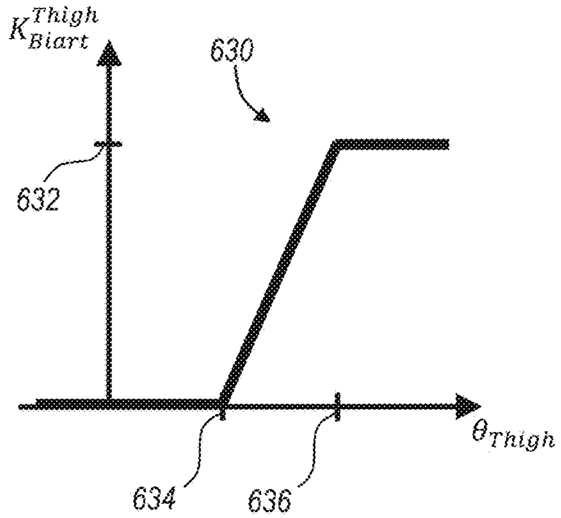

FIG. 6B similarly shows the relationship 630 between the biarticular thigh gain 404 and the thigh orientation 220 and illustrates that the value of the biarticular thigh gain 404 may be dependent on the thigh orientation 220. The biarticular thigh gain 404 may have a maximum value 632 and a minimum value. For example, the maximum value 632 may be approximately 1.0 and the minimum value may be approximately 0, such that the biarticular thigh gain 404 exhibits a value from approximately 0 to approximately 1.0. The maximum value 632 of the biarticular thigh gain 404 may not necessarily be 1.0, but may be a value corresponding to the particular characteristics and/or dimensions of the powered prosthetic leg 101.

The biarticular thigh gain 404 may be variable between a lower threshold 634 and an upper threshold 636 of the thigh orientation 220. The biarticular thigh gain 404 may be at a minimum value when the thigh orientation 220 is at or below the lower threshold 634 and may be at a maximum value 632 when the thigh orientation 220 is at or above the upper threshold 636. Thus, the biarticular thigh gain 404 may be at or near a maximum value at the end of stance phase and the beginning of swing phase. The lower threshold 634 may be set within a range from approximately 1 degree to approximately 15 degrees, or from approximately 2 degrees to approximately 10 degrees, or from approximately 3 degrees to approximately 8 degrees, or from approximately 4 degrees to approximately 6 degrees, or may be set to approximately 5 degrees, or may be set within a range having any two of the foregoing as endpoints. The upper threshold 636 may be set within a range from approximately 5 degrees to approximately 25 degrees, or from approximately 7 degrees to approximately 20 degrees, or from approximately 8 degrees to approximately 15 degrees, or from approximately 10 degrees to approximately 12 degrees, or may be set within a range having any two of the foregoing as endpoints. For example, the lower the upper thresholds 634, 636 may be set to approximately 5 degrees and approximately 10 degrees, respectively.

Thus, in at least some embodiments, the upper and lower thresholds 636, 634 may be set to thigh orientations 220 wherein the residual limb 216 is disposed behind, or posterior to, the torso of the body. By incorporating the flexion knee gain and the flexion thigh gain, this ensures that the biarticular torque component is greatest at the beginning of swing phase when the powered prosthetic leg 101 is off the ground and when the thigh orientation 220 is greatest.

The biarticular thigh gain 404 may be linearly related to the thigh orientation 220 between the upper and lower thresholds 636, 634. Alternatively, the biarticular thigh gain 404 may be linearly related to the thigh orientation 220 over only a portion of the range between the upper and lower thresholds 636, 634 or may have another relationship with the thigh orientation 220, such as an exponential or logarithmic relationship, or a binomial, trinomial, or other polynomial relationship.

The target knee torque 410 may be further determined by the addition of a damping torque 440 (i.e., $T_{Damping}$), such that the target knee torque 410 may be determined by the following relationship: $T_{Knee}=T_{Step\text{-}up}+T_{Biart}+T_{Damping}$. The damping torque 440 may function to smooth out the knee torque signal output to the powered prosthetic leg 101, so as to provide a more comfortable and controllable movement to the user. The damping torque 440 may be proportional to and opposite a prosthetic knee velocity 408, such that the damping torque 440 may be determined by the following relationship: $T_{Damping}=-B\cdot\dot{\theta}_{Knee}$. Thus, the damping torque 440 may work to slow or even out the target knee torque 410 as the absolute value of prosthetic knee velocity 408 increases.

The above relationship also illustrates that the damping torque 440 is proportional to a gain coefficient 406 (i.e. B). FIG. 4 shows that the value of the gain coefficient 406 may depend on the prosthetic knee velocity 408 as well as the thigh orientation 220 and/or the knee orientation 222. The gain coefficient 406 may be mapped to a flexion gain (i.e., $B_{Flex}$) when the prosthetic knee velocity 408 is greater than 0 degrees per second and may be mapped to an extension gain (i.e., $B_{Ext}$) when the prosthetic knee velocity 408 is less than 0 degrees per second.

Figure 7A:
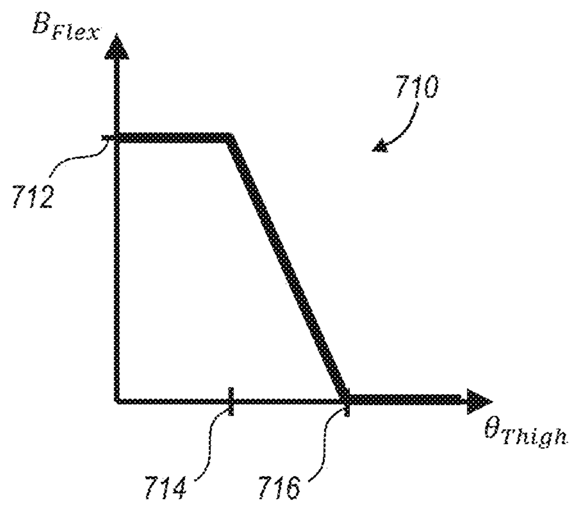
FIGS. 7A-7B illustrate the variability of gain values used to calculate the damping torque.

FIG. 7A shows the relationship 710 between the flexion gain and the thigh orientation 220 and illustrates that the value of the flexion gain may depend on the measured thigh orientation 220. In particular, the flexion gain may be variable between a lower threshold 714 and an upper threshold 716 of the thigh orientation 220. The flexion gain may be at a maximum value 712 when the thigh orientation 220 is at or below the lower threshold 714 and may be at the minimum value when the thigh orientation 220 is at or above the upper threshold 716. For example, the maximum value 712 may be approximately 0.15 and the minimum value may be approximately 0, such that the extension gain exhibits a value from approximately 0 to approximately 0.15. The maximum value 712 of the extension gain may not necessarily be 0.15, but may be a value corresponding to the particular characteristics and/or dimensions of the powered prosthetic leg 101.

The lower threshold 714 may be set within a range from approximately 1 degree to approximately 15 degrees, or from approximately 2 degrees to approximately 10 degrees, or from approximately 3 degrees to approximately 8 degrees, or from approximately 4 degrees to approximately 6 degrees, or may be set to approximately 5 degrees, or may be set within a range having any two of the foregoing as endpoints. The upper threshold 716 may be set within a range from approximately 5 degrees to approximately 25 degrees, or from approximately 7 degrees to approximately 20 degrees, or from approximately 8 degrees to approximately 15 degrees, or from approximately 10 degrees to approximately 12 degrees, or may be set within a range having any two of the foregoing as endpoints. For example, the lower the upper thresholds 714, 716 may be set to approximately 5 degrees and approximately 10 degrees, respectively.

The flexion gain may be linearly related to the thigh orientation 220 between the lower and upper thresholds 714, 716. Alternatively, the flexion gain may be linearly related to the thigh orientation 220 over only a portion of the range between the lower and upper thresholds 714, 716 or may have another relationship with the thigh orientation 220 between the lower and upper thresholds 714, 716, such as an exponential or logarithmic relationship, or a binomial, trinomial, or other polynomial relationship.

Figure 7B:
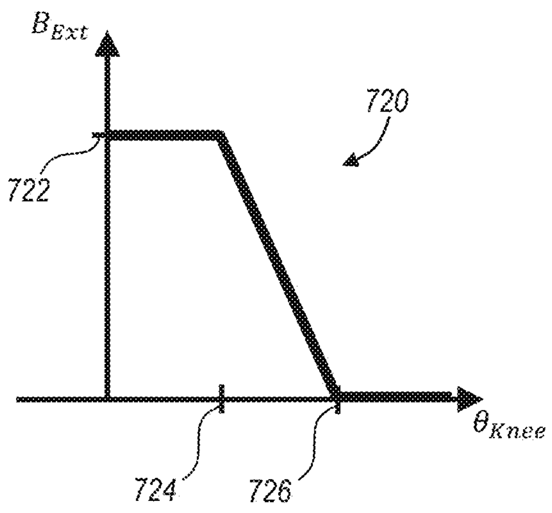

FIG. 7B shows the relationship 720 between the extension gain and the knee orientation 222 and illustrates that the value of the extension gain may be dependent on the knee orientation 222. The extension gain may have a maximum value 722 and a minimum value. For example, the maximum value 722 may be approximately 0.05 and the minimum value may be approximately 0, such that the extension gain exhibits a value from approximately 0 to approximately 0.05. The maximum value 722 of the extension gain may not necessarily be 0.05, but may be a value corresponding to the particular characteristics and/or dimensions of the powered prosthetic leg 101.

The extension gain may be variable between a lower threshold 724 and an upper threshold 726 of the knee orientation 222. The extension gain may be at the maximum value 722 when the knee orientation 222 is at or below the lower threshold 724 and may be at the minimum value when the knee orientation 222 is at or above the upper threshold 726. Thus, the extension gain may be at or near a maximum value at the end of stance phase and the beginning of swing phase when the knee orientation 222 is smallest (i.e., when the powered knee joint 104 is fully flexed), such that the extension knee gain contributes to the dampening of the target knee torque most at the end of stance phase and beginning of swing phase.

The lower threshold 724 may be set within a range from approximately 3 degrees to approximately 18 degrees, or from approximately 5 degrees to approximately 15 degrees, or from approximately 6 degrees to approximately 14 degrees, or from approximately 8 degrees to approximately 12 degrees, or may be set to approximately 10 degrees, or may be set within a range having any two of the foregoing as endpoints. The upper threshold 726 may be set within a range from approximately 10 degrees to approximately 35 degrees, or from approximately 12 degrees to approximately 33 degrees, or from approximately 15 degrees to approximately 30 degrees, or from approximately 18 degrees to approximately 27 degrees, or from approximately 20 degrees to approximately 25 degrees, or may be set within a range having any two of the foregoing as endpoints. For example, the lower and upper thresholds 724, 726 may be set to approximately 10 degrees and 20 degrees, respectively.

The extension gain may be linearly related to the knee orientation 222 between the upper and lower threshold 726, 724. Alternatively, the extension gain may be linearly related to the knee orientation 222 over only a portion of the range between the upper and lower thresholds 726, 724 or may have another relationship with the knee orientation 222, such as an exponential or logarithmic relationship, or a binomial, trinomial, or other polynomial relationship. In this manner, the dampening torque 440 acts to slow and smooth the torque exerted by the powered knee joint 104 throughout the gait cycle.

No Contact State

The volitional controller may be configured in a no contact state when the ground state signal falls below the lower GRF threshold. When the volitional controller is in the no contact state the volitional controller may continue to output a knee torque signal. However, the knee torque signal may not be based on the determination of the target knee torque. Instead, when the volitional controller is in the no contact state the knee torque signal may be based on a desired knee orientation (i.e., $\theta_{Knee}^{Desired}$).

The desired knee orientation may be a knee orientation at the end of swing phase set to prepare the user to begin stance phase of the gait cycle. The desired knee orientation may be defined as the sum of two components, including a minimum jerk trajectory and an adaptive orientation, as illustrated by the following relationship:

$$\theta_{Knee}^{Desired} = \theta_{MJ} + \theta_{Adp}.$$

Figure 8A:
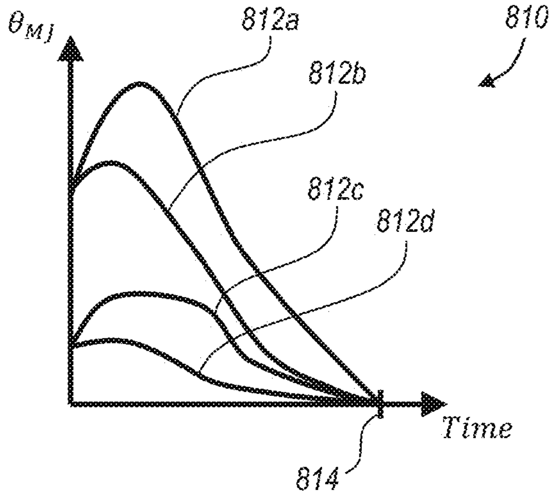
FIG. 8A illustrates various jerk trajectories used to determine a minimum jerk trajectory.

FIG. 8A illustrates the relationship 810 between the minimum jerk trajectory and the desired movement duration, showing multiple jerk trajectories 812*a*, 812*b*, 812*c*, 812*d* that may be considered by the powered knee and prosthetic leg system 100. The minimum jerk trajectory (i.e., $\theta_{MJ}$) may be chosen or determined by a minimum-jerk optimizer so as to select a trajectory exhibiting minimal changes to the angular acceleration of the shank 106 and/or the prosthetic knee velocity, ensuring an even smooth rotation of the shank 106 from a posterior position to an anterior position during the no contact state and/or during swing phase of the gait cycle. The multiple jerk trajectories may be calculated based on the desired movement duration time 814 as measured from the knee orientation at toe-off. The desired movement duration time 814 may be proportional to the duration in which the volitional controller was previously in the contact state.

The adaptive orientation (i.e., $\theta_{Adp}$) may be determined as the product of a synergistic orientation (i.e., $\theta_{syn}$) and an adaptive gain (i.e., $K_{syn}$), and may be determined by the following relationship: $\theta_{Adp}=(K_{syn}\cdot\theta_{syn})$. The synergistic orientation may be proportional to and opposite the knee orientation 222, and may be defined according to the relationship as follows: $\theta_{syn}=-K_{LR}\cdot\theta_{Knee}$. The synergistic orientation may be proportional to a linear relationship multiplier (i.e., $K_{LR}$).

Figure 8B:
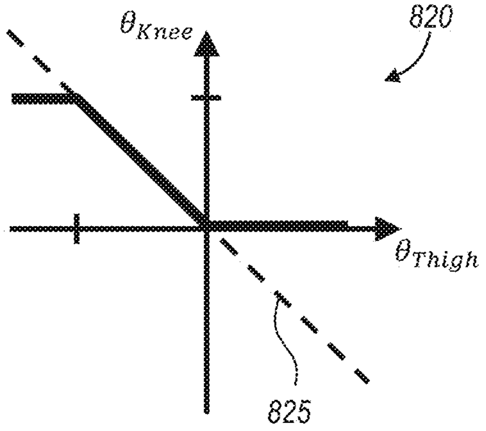
FIG. 8B illustrates the relationship between the thigh orientation and the knee orientation.

FIG. 8B illustrates the relationship 820 between the knee orientation 222 and the thigh orientation 220. In particular, the knee and thigh orientations 222, 220 may be configured to move together, such that over a portion of the available thigh and knee orientations 220, 222, as the thigh orientation 220 decreases from 0 (i.e., as the residual limb 216 moves from a vertical position to a position in front of the torso) the knee orientation 222 may increase from 0 (e.g., the powered knee joint 104 may flex from full extension) at a rate of the thigh orientation 220. This rate, which may also be referred to as the linear relationship multiplier, is illustrated as the slope of the line 825. Thus, the linear relationship multiplier may be constant. The linear relationship multiplier may be set to a value of −0.5, −0.6, −0.7, −0.8, −0.9, −1.0, −1.1, −1.2, −1.3, −1.4, or −1.5, or may be set within a range having any two of the foregoing as endpoints.

Figure 8C:
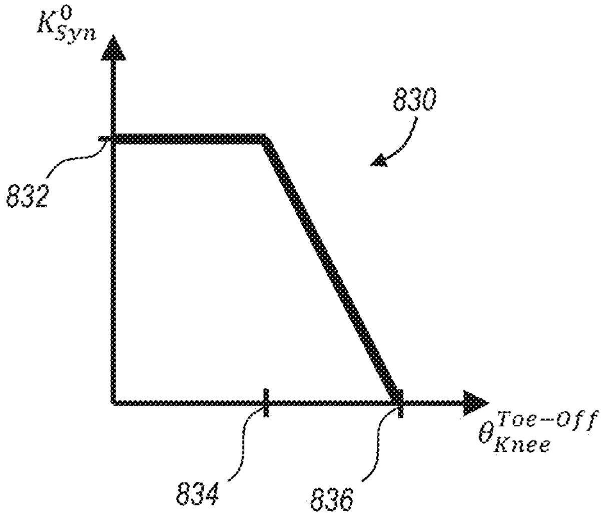
FIG. 8C illustrates the variability of an adaptive gain with respect to the knee orientation.

The adaptive gain may be determined as the sum of an initial adaptive gain (i.e., $K_{Syn}^{0}$) and an adaptive gain change (i.e., $\Delta K_{Syn}$), as in the following relationship: $K_{Syn}=K_{Syn}^{0}+\Delta K_{Syn}$. FIG. 8C illustrates relationship 830, showing that the initial adaptive gain may depend on the knee orientation at toe-off (i.e., $\theta_{Knee}^{Toe\text{-}Off}$). The knee orientation at toe-off may be determined as the knee orientation 222 when the ground state signal falls below a toe-off threshold. The toe-off threshold may be the same as the lower GRF threshold described above, such that the knee orientation at toe-off is determined as the knee orientation 222 at the transition of the volitional controller from the contact state to the no contact state, or as the knee orientation 222 at the transition from stance phase to swing phase.

The initial adaptive gain may have a maximum value 832 and a minimum value. For example, the maximum value 832 may be approximately 1 and the minimum value may be approximately 0, such that the initial adaptive gain exhibits a value from approximately 0 to approximately 1. The maximum value 832 of the initial adaptive gain may not necessarily be set to a value of 1, but may be set at a value corresponding to the particular characteristics and/or dimensions of the powered prosthetic leg 101.

The initial adaptive gain may be variable between a lower threshold 834 and an upper threshold 836 of the knee orientation at toe-off. The initial adaptive gain may be at the maximum value 832 when the knee orientation at toe-off is at or below the lower threshold 834 and may be at the minimum value when the knee orientation at toe-off is at or above the upper threshold 836. Thus, the initial adaptive gain may be at or near a maximum value at the end of stance phase and the beginning of swing phase. The lower threshold 834 may be set within a range from approximately 3 degrees to approximately 15 degrees, or from approximately 5 degrees to approximately 12 degrees, or from approximately 6 degrees to approximately 10 degrees, or from approximately 7 degrees to approximately 9 degrees, or may be set to approximately 8 degrees or may be set within a range having any two of the foregoing as endpoints. The upper threshold 836 may be set within a range from approximately 8 degrees to approximately 25 degrees, or from approximately 10 degrees to approximately 20 degrees, or from approximately 12 degrees to approximately 18 degrees, or may be set to approximately 15 degrees, or may be set within a range having any two of the foregoing as endpoints. For example, the lower and upper thresholds 834, 836 may be set to approximately 8 degrees and 15 degrees, respectively.

The initial adaptive gain may be linearly related to the knee orientation at toe-off between the upper and lower threshold 836, 834. Alternatively, the initial adaptive gain may be linearly related to the knee orientation at toe-off over only a portion of the range between the upper and lower thresholds 836, 834 or may have another relationship with the knee orientation at toe-off, such as an exponential or logarithmic relationship, or a binomial, trinomial, or other polynomial relationship.

The adaptive gain change ensures that the adaptive gain is updated continuously during the no contact state. The adaptive gain change may also vary. The adaptive gain change may be dependent on the thigh orientation 220 and a thigh velocity (i.e., $\dot{\theta}$Thigh). When the thigh orientation is in a range from approximately negative 10 degrees to approximately negative 35 degrees and when the thigh velocity is greater than negative 50 degrees per second the adaptive gain change may be calculated by the following relationship: $\Delta K_{syn(n+1)}=\Delta K_{Syn(n)}-0.008$. The terms n and n+1 may refer to moments at which the adaptive gain change is calculated, such that the adaptive gain change is dependent on previous calculations of the adaptive gain change. Although the adaptive gain change is decreased by 0.008 at each moment of calculation, the adaptive gain change may be decreased (or increased) by another value according to the needs of the user.

When the thigh orientation is less than or equal to approximately negative 35 degrees (when the residual thigh is angle far in front of the user's torso) and the thigh velocity is less than or equal to approximately negative 20 degrees per second, the adaptive gain change may be calculated according to the following relationship: $\Delta K_{Syn(n+1)}=\Delta K_{Syn(n)}+0.016$. Similar to the adaptive gain change relationship described above, although the adaptive gain change is increased by 0.016 at each moment of calculation, the adaptive gain change may be increased (or decreased) by another value according to the needs of the user. Thus, the desired knee orientation may be determined as a combination of the minimum jerk trajectory and the adaptive orientation to provide the desired end knee orientation at the end of swing phase in preparation for the user to begin stance phase in the gait cycle.

Additional Terms & Definitions

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, less than 1%, less than 0.1%, or less than 0.01% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

The embodiments disclosed herein should be understood as comprising/including disclosed components, and may therefore include additional components not specifically described. Optionally, the embodiments disclosed herein are essentially free or completely free of components that are not specifically described. That is, non-disclosed components may optionally be completely omitted or essentially omitted from the disclosed embodiments.

It will also be appreciated that embodiments described herein may also include properties and/or features (e.g., ingredients, components, members, elements, parts, and/or portions) described in one or more separate embodiments and are not necessarily limited strictly to the features expressly described for that particular embodiment. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

Example Aspects

The following clauses provide a non-exhaustive list of example aspects of the disclosed volitional controller for a powered knee prosthesis:

Clause 1. A volitional controller for a powered knee prosthesis, comprising: one or more processors, and one or more hardware storage devices having instructions stored thereon that are executable by the one or more processors to cause the controller to at least: determine a knee orientation and an ankle torque; determine a target knee torque based on the knee orientation and ankle torque; output a knee torque signal for controlling a powered knee joint of a powered knee prosthesis, wherein the controller does not classify ambulation activity or switch between activity-specific controllers according to walking, stair ascent, or stair descent activities.

Clause 2. The volitional controller of clause 1, wherein the instructions further cause the controller to determine a thigh orientation and a prosthetic knee velocity.

Clause 3. The volitional controller of any preceding clause, wherein the target knee torque is determined via summing a step-up torque and a biarticular torque.

Clause 4. The volitional controller of clause 3, wherein the biarticular torque is proportional to the ankle torque.

Clause 5. The volitional controller of clause 4, wherein the biarticular torque is further proportional to a biarticular knee gain and a biarticular thigh gain.

Clause 6. The volitional controller of clause 5, wherein the biarticular knee gain is dependent on a knee orientation and is variable between a lower threshold and an upper threshold of the knee orientation.

Clause 7. The volitional controller of clause 5 or clause 6, wherein the biarticular thigh gain is dependent on a thigh orientation and is variable between a lower threshold and an upper threshold of the thigh orientation.

Clause 8. The volitional controller of any of clauses 3-7, wherein the target knee torque is further determined adding a damping torque.

Clause 9. The volitional controller of clause 8, wherein the damping torque is proportional to and opposite a prosthetic knee velocity.

Clause 10. The volitional controller of any preceding clause, wherein the instructions further cause the volitional controller to: receive a ground state signal; and configure the controller in a contact state or a no contact state; wherein when the controller is in a contact state the knee torque signal is based on the target knee torque.

Clause 11. The volitional controller of clause 10, wherein when the controller is in a no contact state the knee torque signal is based on a desired knee orientation.

Clause 12. The volitional controller of clause 11, wherein the desired knee orientation is determined by summing a minimum jerk trajectory and an adaptive orientation.

Clause 13. The volitional controller of clause 12, wherein the adaptive orientation is determined as a product of a synergistic orientation and an adaptive gain.

Clause 14. A powered knee and prosthetic leg system configured to provide volitional control to a user, the system comprising: a powered knee prosthesis; and the volitional controller of any preceding clause.

Clause 15. The powered knee and prosthetic leg system of clause 14, wherein the powered knee prosthesis comprises: a shank having a proximal and a distal end; a prosthetic foot connected to the distal end of the shank; a powered knee joint connected to the proximal end of the shank; and a socket configured to receive a residual limb of a user, wherein the socket is connected to the powered knee joint.

Clause 16. The powered knee and prosthetic leg system of clause 14 or clause 15, wherein the powered knee prosthesis comprises a GRF sensor and an IMU sensor.

Clause 17. The powered knee and prosthetic leg system of any of clauses 14-16, wherein the powered knee prosthesis is configured to enable a user to walk on even and/or inclined surfaces and to ascend and/or descend stairs.

Clause 18. A method for controlling a powered knee prosthesis, comprising: determining a knee orientation and an ankle torque; determining a target knee torque based on the knee orientation and ankle torque; and outputting a knee torque signal for controlling a powered knee joint of the powered knee prosthesis.

Clause 19. The method of clause 18, further comprising determining a thigh orientation and a prosthetic knee velocity.

Clause 20. The method of clause 18 or clause 19, further comprising configuring a volitional controller in a contact state or a no contact state and basing the knee torque signal on the target knee torque when the volitional controller is in the contact state.

The invention claimed is:

1. A system for providing volitional control to a powered knee prosthesis, comprising:

a powered knee prosthesis comprising a powered knee joint; and a volitional controller comprising one or more processors and one or more hardware storage devices having instructions stored thereon that are executable by the one or more processors to cause the controller to at least:

determine a knee orientation and an ankle torque;

determine a target knee torque based on the knee orientation and ankle torque, wherein the target knee torque is determined by summing (i) a step-up torque calculated from measured knee orientation wherein the step-up torque increases from a lower knee orientation threshold to a maximum value and then decreases toward an upper knee orientation threshold, and (ii) a biarticular torque defined as a knee flexion torque that is proportional to a measured ankle plantarflexion torque; and output a knee torque signal to the powered knee joint of the powered knee prosthesis to adjust the powered knee joint toward the target knee torque, wherein the controller does not classify ambulation activity or switch between activity-specific controllers according to walking, stair ascent, or stair descent activities.

2. The system of claim 1, wherein the instructions further cause the controller to determine a thigh orientation and a prosthetic knee velocity.

3. The system of claim 1, wherein the biarticular torque is further determined by multiplying the measured ankle plantarflexion torque with a biarticular knee gain and a biarticular thigh gain, wherein:

the biarticular knee gain has a value dependent on measured knee orientation, with a maximum value at or below a lower knee orientation threshold and a minimum value at or above an upper knee orientation threshold; and the biarticular thigh gain has a value dependent on measured thigh orientation, with a minim value at or below a lower thigh orientation threshold and a maximum value at or above an upper thigh orientation threshold.

4. The system of claim 1, wherein the target knee torque is further determined by adding a damping torque.

5. The system of claim 4, wherein the damping torque is proportional to and opposite a prosthetic knee velocity.

6. The system of claim 1, wherein the instructions further cause the volitional controller to:

receive a ground state signal; and configure the controller in a contact state or a no contact state;

wherein the knee torque signal is configured to adjust the powered knee joint toward the target knee joint when the controller is in the contact state.

7. They system of claim 6, wherein when the controller is in the no contact state the knee torque signal is configured to adjust the powered knee joint toward a desired knee orientation, the desired knee orientation being determined by summing a minimum jerk trajectory and an adaptive orientation, wherein:

the minimum jerk trajectory is a trajectory selected to minimize changes to angular acceleration of a shank of the powered knee prosthesis; and the adaptive orientation is a product of a synergistic orientation angle and an adaptive gain, wherein (i) the synergistic orientation angle is proportional to and opposite the knee orientation, and (ii) the adaptive gain is based on a toe-off knee orientation measured at the transition from the contact state to the no contact state, the adaptive gain having a higher value at lower toe-off knee orientation and a lower value at higher toe-off knee orientation.

8. The system of claim 1, wherein the powered knee prosthesis comprises:

a shank having a proximal and a distal end;

a prosthetic foot connected to the distal end of the shank;

a powered knee joint connected to the proximal end of the shank; and a socket configured to receive a residual limb of a user, wherein the socket is connected to the powered knee joint.

9. The powered-kace-and-prosthetic log-system of claim 1, wherein the powered knee prosthesis comprises a ground reaction force (GRF) sensor and an inertial measurement unit (IMU).

10. The system of claim 1, wherein the powered knee prosthesis is configured to enable a user to walk on even and/or inclined surfaces and to ascend and/or descend stairs.

11. A method for controlling a powered knee prosthesis, comprising:

determining a knee orientation and an ankle torque;

determining a target knee torque based on the knee orientation and ankle torque, wherein the target knee torque is determined by summing (i) a step-up torque that is related to knee orientation wherein the step-up torque increases from a lower knee orientation threshold to a maximum value and then decreases toward an upper knee orientation threshold, and (ii) a biarticular torque defined as a knee flexion torque that is proportional to a measured ankle plantarflexion torque; and outputting a knee torque signal to a powered knee joint of the powered knee prosthesis to adiost powered knee joint toward the target knee torque.

12. The method of claim 11, further comprising determining a thigh orientation and a prosthetic knee velocity.

13. The method of claim 11, further comprising configuring a volitional controller in a contact state or a no contact state and basing the knee torque signal on the target knee torque when the volitional controller is in the contact state.

14. A system for providing volitional control to a powered knee prosthesis, comprising:

a powered knee prosthesis comprising a powered knee joint;

and a volitional controller comprising one or more processors and one or more hardware storage devices having instructions stored thereon that are executable by the one or more processors to cause the controller to at least:

receive a ground state signal indicating a transition from a contact state to a no contact state;

determine a toe-off knee orientation defined as the knee orientation measured at the transition from the contact state to the no contact state;

and output a knee torque signal to the powered knee joint of the powered knee prosthesis to adjust the powered knee joint toward a desired knee orientation, the desired knee orientation being determined by summing a minimum jerk trajectory and an adaptive orientation, wherein the minimum jerk trajectory is a trajectory selected to minimize changes to angular acceleration of a shank of the powered knee prosthesis, wherein the adaptive orientation is a product of a synergistic orientation angle and an adaptive gain, wherein (i) the synergistic orientation angle is proportional to and opposite a current knee orientation, and (ii) the adaptive gain is based on the toe-off knee orientation, with a higher value at lower toe-off knee orientation and a lower value at higher toe-off knee orientation.

15. The system of claim 14, wherein the controller does not classify ambulation activity or switch between activity-specific controllers according to walking, stair ascent, or stair descent activities.

* * * * *